United States Patent [19]

Tiwari

[11] Patent Number: 4,582,059

[45] Date of Patent: Apr. 15, 1986

[54] TONGUE CLEANING INSTRUMENT

[76] Inventor: Sandra J. Tiwari, 1600 Ann Cir., Mechanicsville, Md. 20659

[21] Appl. No.: 609,986

[22] Filed: May 14, 1984

[51] Int. Cl.[4] .................... A61B 17/22; A45D 44/18
[52] U.S. Cl. .................................... 128/304; 132/84 A
[58] Field of Search ............ 128/62 A, 304; 132/1 R, 132/84 R, 84 A; 15/227, 210 A, 111

[56] References Cited

U.S. PATENT DOCUMENTS

| | | | |
|---|---|---|---|
| D. 238,108 | 12/1975 | Cooke | D24/23 |
| D. 253,789 | 12/1979 | Gupta | D24/23 |
| D. 259,209 | 5/1981 | Gautama | D24/10 |
| D. 267,508 | 1/1983 | Gupta | D24/2 |
| 697,336 | 4/1902 | Hagerty | 128/304 |
| 1,533,123 | 4/1925 | Lewis | 128/304 |
| 1,658,706 | 2/1928 | Carrott | 128/304 |
| 1,701,616 | 2/1929 | Gross | 128/304 |
| 1,728,956 | 9/1929 | Darmitzel | 128/304 |
| 1,741,143 | 12/1929 | Chin | 128/304 |
| 1,811,775 | 6/1931 | Barkwill | 128/304 |
| 1,851,396 | 3/1932 | Mabry | 128/304 |
| 1,891,864 | 12/1932 | Barrett | 128/304 |
| 1,893,524 | 1/1933 | Shanley | 128/304 |
| 2,049,956 | 8/1936 | Greenberg | 128/304 |
| 2,218,072 | 10/1940 | Runnels | 128/304 |
| 2,405,029 | 7/1946 | Gallanty et al. | 128/304 |
| 2,543,999 | 3/1951 | Voss | 128/304 |
| 2,574,654 | 11/1951 | Moore | 15/111 |
| 3,254,356 | 6/1966 | Yao et al. | 128/304 |
| 3,683,924 | 8/1972 | Louie | 128/304 |
| 3,811,447 | 5/1974 | Weber | 128/304 |
| 3,890,964 | 6/1975 | Castanedo | 128/62 R |
| 3,943,592 | 3/1976 | Bhaskar | 15/160 |

OTHER PUBLICATIONS

Gilmore et al., "Effect of Tongue Brushing on Plaque Bacteria", Oral Surg., Aug. 1973, pp. 201–204.
Gross et al., "Effects of Tongue Brushing on Tongue Coating and Dental Plaque Scores", J Dent Res, Nov.–Dec., 1974, vol. 54, No. 6, p. 1236.
Hyde et al., "Tongue Brushing, Dentifrice, and Age Effects on Taste and Smell", J Dent Res, Oct. 1981, vol. 60, No. 10, pp. 1730–1734.
Christen and Swanson, "Oral Hygiene: A History of Tongue Scraping and Brushing", JADA, vol. 96, Feb. 1978, pp. 215–119.
Jacobson et al., "Oral Physiotherapy of the Tongue and Palate: Relationship to Plaque Control", JADA, vol. 87, Jul. 1973, pp. 134–139.
Gilmore et al., "Effect of Tongue Brushing on Bacterial Population", JSCDA, vol. 39, Nov. 1971, pp. 893–895.
Mangle, "Effects of Daily Mechanical Tongue Scraping Versus Daily Mechanical Tongue Brushing on Bacterial Flora", Incidentals, May, 1983, pp. 13–16.

Primary Examiner—Gene Mancene
Assistant Examiner—Carolyn A. Harrison
Attorney, Agent, or Firm—Lowe, King, Price & Becker

[57] ABSTRACT

A hygienic tongue scraping and massage instrument for freeing and removing pathogenic foreign matter entrapped in upper surfaces of the tongue comprises a pair of elongated handles and a generally straight cross bar formed with a scraping edge and having opposite ends connected respectively to forward ends of the handles. Connections of the opposite ends with the forward ends establish corners so that the scraping edge extends continuously along the cross bar to intersect the corners. Each handle is preferably rectangular in cross section with the cross bar being of triangular cross section and tapered downwards to form the scraping edge. The corners are generally sector or triangular shaped so that the handles and cross bar are sufficiently rigid to resist torsional flexing of the handles and minimize the tendency of the scraping edge to partially disengage the tongue as the instrument is brought forward by the user out of the oral cavity.

10 Claims, 4 Drawing Figures

U.S. Patent Apr. 15, 1986 4,582,059
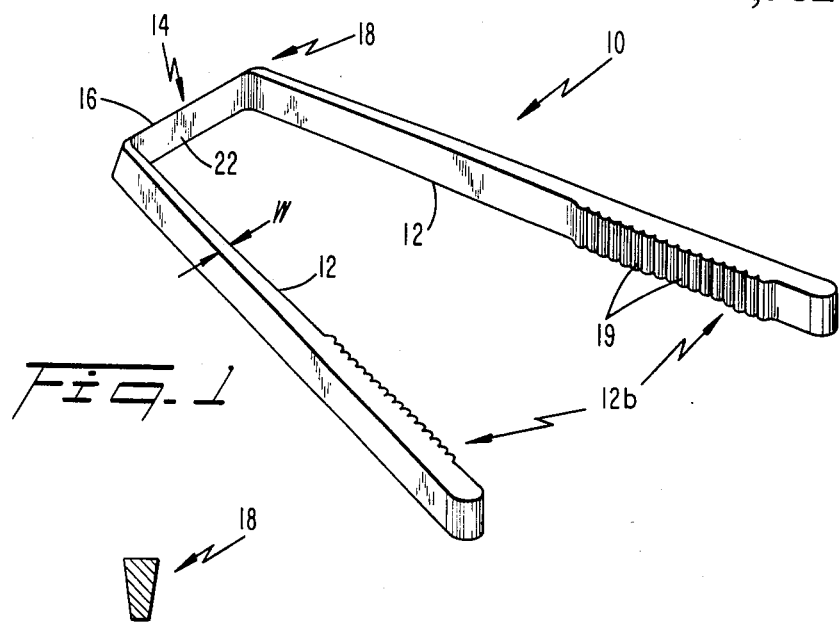
Fig. 1
Fig. 4
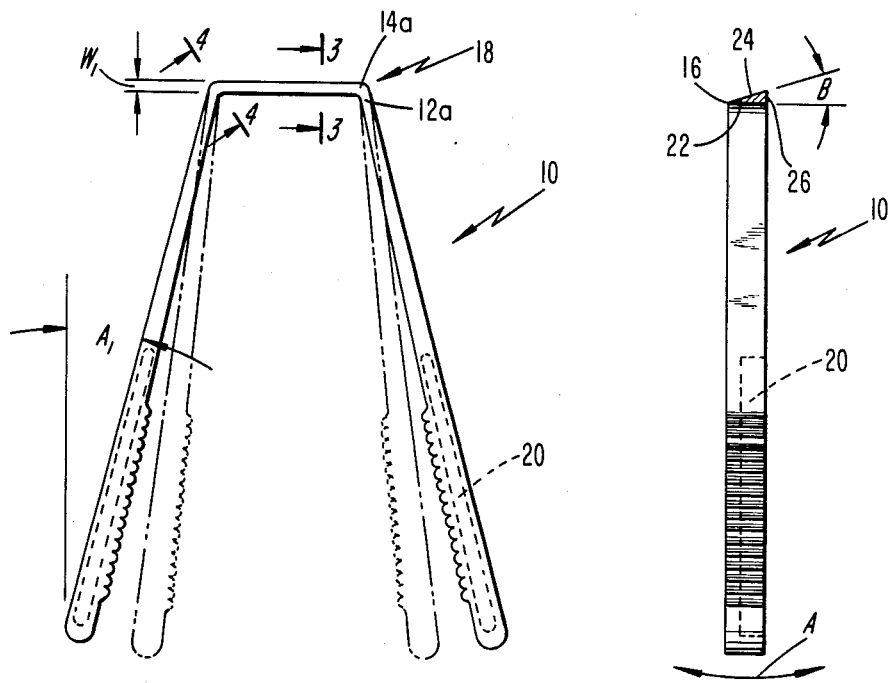
Fig. 2
Fig. 3

TONGUE CLEANING INSTRUMENT

TECHNICAL FIELD

The present invention generally relates to oral hygiene apparatus and, more particularly, to a tongue scraper for removing plaque and bacteria from surfaces of the tongue.

BACKGROUND ART

Studies have shown that the dorsum of the tongue is one of the main foci of microorganisms in the oral cavity. These microorganisms are responsible for a variety of harmful oral diseases and plaque build up. However, studies have also shown that the total bacterial count on the dorsum of the tongue can be reduced by as much as 50% after only one day of mechanical tongue scraping, as compared to one week of tongue brushing that would be necessary to achieve the same result.

Mechanical tongue scrapers are well known for scraping to clean the dorsal or upper surface of the tongue and generally comprise a handle having formed at one end a cross bar with a scraping edge. To clean the tongue, the handle is inserted into the mouth so that the scraping edge contacts the back or inner end of the tongue with the handle protruding from the mouth and held to apply a firm downward force. The instrument held in this position is drawn forwardly along the tongue so that foreign bacteria stripped from the tongue by the scraping edge is propelled upwardly from the edge to collect on a surface of the cross bar formed adjacent the edge. Of course, once the instrument is removed from the mouth after cleaning the tongue, the stripped foreign matter is washed from the scraper bar and the cleaning operation is then repeated. More specifically, because of the width of the tongue relative to the length of the scraping edge, three cleaning steps are usually performed. In the first step, the scraping edge is applied to clean sides or convex marginal portions of the tongue in separate cleaning strokes. The center depressed area (which merges laterally through upwardly and outwardly sloping areas into the convext marginal portions) is then cleaned. If this operation is performed daily or at other frequent intervals, harmful accumulations of foreign matter can be avoided, tongue pipillae will be maintained in a healthy condition, and the discomfort and objectionable odor from such harmful accumulations can be avoided.

Tongue scrapers of which I am aware generally include either one or two handles. With single handle models, one end of the handle is formed with a pair of bifurcated arms with the transverse scraping bar connected to free ends thereof. A problem associated with this single handle instrument is that the handle which extends along the central longitudinal axis of the instrument is normally placed on the central portion of the tongue when the scraping edge initially contacts the back of the tongue. Contact between the handle and tongue causes undesirable and involuntary upward flexing of the tongue tending to disengage the scraping edge from the tongue. Thus, with single handle models, the scraping edge is elevated above certain portions of the tongue due to involuntary tongue flexing caused by the single handle, resulting in incomplete tongue cleaning.

Double handle tongue scrapers generally comprise a thin strip of flexible resilient material (e.g., metal) prebent into a U-shape to establish a pair of handles connected by a central curved tongue scraping portion. Since the handles diverge outward from the curved scraping portion, these handles usually do not contact the tongue during scraping, avoiding the aforesaid problem associated with single handle instruments. However, since both handles are gripped to draw the scrapping portion forwardly along the tongue, disengagement of portions of the scraping edge with the tongue frequently occurs due to the inherent flexibility of the handles. In other words, as the gripped handles are brought forward out of the mouth during cleaning, there is a tendency by the user to exert a twisting force on the handles causing the aforesaid separation. Furthermore, since there is a continuous curvature between the handles and the scraping portions, portions of the handles formed adjacent the scraping portion contact the tongue causing the aforesaid involuntary flexing of the tongue to occur, resulting in partial separation of the scraping edge with the tongue surface.

It is accordingly an object of the present invention to provide a tongue cleaning and scraping instrument to extend preventative hygiene of the oral cavity to effective cleaning and massaging of the dorsal mucosa so as to loosen and remove entrapped pathogenic foreign matter and, through abrasive engagement, maintain the papillae in a healthy condition.

Another object of the present invention is to provide a tongue scraper having a pair of handles arranged to avoid contact with the tongue during tongue cleaning so that the scraping edge remains in full contact with portions of the tongue as the handles are brought forward by the user out of the mouth.

Still another object is to provide a tongue scraper having handles that are easily and comfortably gripped by the user and are configured to resist twisting by the user so that the scraping edge remains in complete contact with desired portions of the tongue.

Yet a further object is to provide a tongue scraper wherein the handles are configured to maximize the effective length of the scraping edge that resists the tendency to separate from portions of the tongue during cleaning.

DISCLOSURE OF THE INVENTION

A tongue scraper, in accordance with the present invention, comprises a pair of elongated handles and a generally straight cross bar formed with a scraping edge. The cross bar includes opposite ends connected respectively to forward ends of the handles. Connections of the opposite ends with the forward ends establish corners so that the scraping edge extends continuously along the cross bar across the full length thereto to intersect the corners.

Each handle is preferably of rectangular cross section and has a width progressively decreasing towards the cross bar. The cross bar extends generally in the plane of the handles and has an inner wall and an outer wall tapered downwards to establish with the inner wall the scraping edge. An upper wall of the cross bar extends generally parallel to and is of greater width than the scraping edge. The uppe wall is also of greater width than portions of the handle formed adjacent the corners. The cross section of each corner is thus generally triangular or sector shaped having a base coplanar with the upper wall of the cross bar. The resulting formation of corners connecting the handles to the cross bar enables the scraper to resist torsional movement tending to be caused by uneven gripping force applied by the user to move the scraper forward out of the oral cavity so that the scraping edge remains in contact with desired portions of the tongue without separation therefrom.

In accordance with other aspects of the invention, each handle preferably diverges to form an angle with the cross bar of approximately 103° to 105°. The divergent handles thus tend to remain out of contact with the tongue during cleaning. Each handle preferably has a hollow cavity formed in gripping ends thereof to reduce the weight of the handle. The hollow cavities extend through each handle approximately one half the length thereof. The gripping ends of the handle are preferably formed with gripping ridges.

Additional objects, advantages and novel features of the invention will be set forth in detail in part in the description which follows and in part will become apparent to those skilled in the art upon examination of the drawing, or may be learned by practice of the invention. The objects and advantages of the invention may be realized and obtained by means of the instrumentalities and combinations particularly pointed out in the appended claims.

BRIEF DESCRIPTION OF THE DRAWING

FIG. 1 is a perspective view of a tongue scraper according to the present invention;

FIG. 2 is a top elevational view of the tongue scraper of FIG. 1;

FIG. 3 is a sectional view taken along the line 3—3 of FIG. 2; and

FIG. 4 is a sectional view taken along the line 4—4 of FIG. 2 illustrating the cross section of the corners formed between the handles and scraping bar.

BEST MODE FOR CARRYING OUT THE INVENTION

Referring to FIG. 1, tongue scraper 10, preferably formed of a suitable generally rigid material, comprises a pair of elongate handles 12 and a generally straight cross bar 14 formed with a scraping edge 16. Cross bar 14 has opposite ends 14a joined respectively to forward ends 12a at the handles to establish corners 18. Scraping edge 16 extends continuously the full length of bar 14 to intersect corners 18, establishing a large scraping region therebetween engageable with the dorsum of the tongue (not shown) as described below. Scraping edge 16 does not intersect outer surfaces of corners 18, as best illustrated in FIG. 1, so that the corners do not form cutting edges that might otherwise injure the tongue or oral cavity. Scraper 10 is uniquely configured in accordance with other features discussed below so that handles 12 remain complanar with bar 14, minimizing torsional flexing of the handles that might otherwise cause undesirable partial separation of edge 16 with the tongue during cleaning.

More specifically, with reference to FIGS. 2 and 3, scraper 10 is made of plastic molded so that handles 12 and cross bar 14 are of unitary construction. Each handle is generally rectangular in cross section and has a width W progressively decreasing towards cross bar 14. Gripping ends 12b of the handles are formed with gripping ridges 19 and hollow cavities 20 that preferably extend longitudinally a distance of one-half the handle length to reduce the weight of the gripping ends.

The excellent gripping characteristics afforded by ridges 19 and the wider gripping ends 12b (relative to ends 12a) prevent slippage of the instrument from the user's hands during cleaning. The reduced weight provided by cavities 20 resists the tendency of the user to pivot handles 12 downward as the instrument is brought forward through the oral cavity during cleaning, thereby preventing undesirable separation of edge 16 with the tongue.

Cross bar 14 has an inner wall 22 and an outer wall 24 tapered downwards to establish edge 16 with the inner wall. An upper wall 26 of bar 14 extends generally parallel to scraping edge 16 and is preferably of greater width W1 than ends 12a of each handle formed adjacent corners 18 for reasons discussed below. Bar 14 is thus triangular in cross section (see FIG. 3) and merges into corners 18 through ends 14a so that the overall cross section of each corner is generally triangular of sector shaped as best shown in FIG. 4. The increased mass of bar 14 (i.e., above edge 16) provided by the triangular cross section cooperates with cavities 20 in handles 12b to prevent disengagement of the edge from the tongue by exerting a greater scraping force tending to keep the edge pressed against the tongue.

The unique configuration of scraper 10 provided by the cross sectional shapes of handles 12, cross bar 14 and corners 18 results in a tongue cleaner having a maximum length scraping edge 16 that resists the tendency to pivot out of contact with surfaces of the tongue during cleaning. To explain, corners 18 and longitudinally divergent handles 12 provide maximum clearance between the handles and tongue when the instrument is initially positioned within the oral cavity with edge 16 pressing against the back or inner end of the tongue. In this manner, the tongue does not involuntarily flex to push the handles off the tongue, as occurs in various prior art cleaning devices of which I am aware, so that edge 16 fully engages the tongue. Of course, as best shown in FIG. 2, handles 12 are sufficiently flexible within the plane of cleaner 10 so that they can be pivoted when necessary into the phantom line position shown in FIG. 2 depending upon the specific contours of the user's oral cavity. However, due to the mass of plastic or like material establishing the cross sectional shapes of handles 12, bar 14 and corners 18 as aforesaid, scraper 10 of the invention tends to resist the tendency of the handles to pivot in the direction of arrow A (FIG. 3) out of the plane in which the handles and cross bar normally lie. Thus, torsional flexing of the handles during cleaning is minimized preventing partial or complete separation of edge 16 with surfaces of the tongue.

Because of the progressively decreasing width W of each handle 12, gripping ends 12b provide reliable gripping conditions for proper cleaning while the narrower width ends 12a proximate edge 16 minimize the extent of intrusion of scraper 10 into the oral cavity, particularly when edge 16 is initially pressed against the back of the tongue, so that gagging is avoided without sacrificing the effective length of scraping edge 16 or the ability of the handles and cross bar to resist torsional movement.

The foregoing description of the preferred embodiment of the invention has been presented for purposes of illustration and description. It is not intended to be exhaustive or to limit the invention to the precise form disclosed, and obviously many modifications and variations are possible in light of the above teaching. This embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A tongue scraper, comprising a pair of elongate handles and a generally straight cross bar formed with a scraping edge and having opposite ends connected respectively to forward ends of the handles, said forward ends being generally straight portions, wherein connections of said opposite ends with said forward ends establish corners so that the scraping edge extends continuously along the cross bar to intersect the corners, and wherein said straight portions form an obtuse angle with said cross bar to maintain said straight portions out of contact with the tongue during use of the scraper.

2. The scraper of claim 1, wherein said cross bar extends generally in the plane of the handles.

3. The scraper of claim 2, wherein each handle is generally rectangular in cross section and has a width progressively decreasing towards the cross bar.

4. The scraper of claim 3, wherein said cross bar has an inner wall and an outer wall tapered downwards to establish with the inner wall said scraping edge, an upper wall of said cross bar extending generally parallel to and of greater width than the scraping edge, said upper wall also being of greater width than portions of each handle formed adjacent the corners.

5. The scraper of claim 4, wherein the cross section of each corner is generally triangular or sector shaped having a base coplanar with the upper wall of said cross bar, the cross section of each corner cooperating with the cross sections of the cross bar and each handle to resist torsional flexing of the scraper tending to be caused by inadvertent force applied by the user to the gripping handles during cleaning that tends to cause one or both handles to move in a direction perpendicular to the plane of the handles and cross bar.

6. The scraper of claim 5, wherein each handle diverges to form an angle with the cross bar of approximately 103° to 105°.

7. The scraper of claim 4, wherein the outer and inner wall of the cross bar form an angle of approximately 15° with each other.

8. The scraper of claim 1, wherein a gripping end of each handle is formed with a hollow cavity to reduce the weight of the handle and thereby resist the tendency of the user to move the handles downward into contact with portions of the oral cavity as the scraper is moved forward through the oral cavity by the user.

9. The scraper of claim 8, wherein each gripping end is formed with gripping ridges.

10. The scraper of claim 8, wherein said hollow cavities respectively extend longitudinally through each handle approximately one-half the length thereof.

* * * * *